(12) United States Patent
Constandt

(10) Patent No.: US 11,093,509 B2
(45) Date of Patent: Aug. 17, 2021

(54) DATA PROCESSING SYSTEM FOR CURATING SEARCH RESULT FACETS

(71) Applicant: ONTOFORCE NV, Ghent (BE)

(72) Inventor: Hans Constandt, Dilbeek (BE)

(73) Assignee: ONTOFORCE NV, Ghent (BE)

( * ) Notice: Subject to any disclaimer, the term of this patent is extended or adjusted under 35 U.S.C. 154(b) by 841 days.

(21) Appl. No.: 15/576,437

(22) PCT Filed: May 19, 2016

(86) PCT No.: PCT/EP2016/061298
§ 371 (c)(1),
(2) Date: Nov. 22, 2017

(87) PCT Pub. No.: WO2016/188861
PCT Pub. Date: Dec. 1, 2016

(65) Prior Publication Data
US 2018/0157716 A1    Jun. 7, 2018

(30) Foreign Application Priority Data
May 26, 2015 (EP) .................................. 15169134

(51) Int. Cl.
| G06F 16/2457 | (2019.01) |
| G06F 16/248 | (2019.01) |
| G06F 16/28 | (2019.01) |
| G06F 16/332 | (2019.01) |
| G06F 16/338 | (2019.01) |
| G16H 10/20 | (2018.01) |
| G16H 20/10 | (2018.01) |

(52) U.S. Cl.
CPC ...... *G06F 16/24575* (2019.01); *G06F 16/248* (2019.01); *G06F 16/285* (2019.01); *G06F 16/338* (2019.01); *G06F 16/3325* (2019.01); *G16H 10/20* (2018.01); *G16H 20/10* (2018.01)

(58) Field of Classification Search
CPC ............ G06F 16/24575; G06F 16/285; G06F 16/338; G06F 16/3325; G06F 16/248; G16H 20/10; G16H 10/20
See application file for complete search history.

(56) References Cited

U.S. PATENT DOCUMENTS

| 2007/0118542 A1 | 5/2007 | Sweeney |
| 2007/0233654 A1 | 10/2007 | Karlson et al. |
| 2008/0086451 A1 | 4/2008 | Torres et al. |
| 2008/0243779 A1 * | 10/2008 | Behnen ............... G06F 16/9032 |
| 2009/0198675 A1 | 8/2009 | Mihalik et al. |
| 2013/0035995 A1 * | 2/2013 | Patterson ............... G06Q 10/10 705/14.4 |

(Continued)

OTHER PUBLICATIONS

Extended European Search Report from EP Application No. EP 15169134, dated Nov. 16, 2015.

(Continued)

*Primary Examiner* — Tamara T Kyle
*Assistant Examiner* — Lahcen Ennaji
(74) *Attorney, Agent, or Firm* — Workman Nydegger

(57) ABSTRACT

A data processing system for updating search result facets comprises a facet linking module which is configured to update a search result facet and corresponding facet categories in view of a non-linked search result property.

15 Claims, 13 Drawing Sheets

(56) References Cited

U.S. PATENT DOCUMENTS

2013/0054569 A1* 2/2013 Mo ................. G06F 16/248
707/722
2016/0085814 A1* 3/2016 Fukuda ............ G06F 16/3328
707/740
2016/0224994 A1* 8/2016 Packer ............. G06Q 30/0201

OTHER PUBLICATIONS

International Search Report from PCT Application No. PCT/EP2016/061298, dated Jun. 13, 2016.

* cited by examiner dB1 record table:

| Record ID | Record Title | Type | Phase | Success rate | ... |
|---|---|---|---|---|---|
| 1001 | Drug A | Interventional | Phase 2 | 66% | ... |
| 1002 | Drug B | Interventional | Phase 1 | 76% | ... |
| 1003 | Drug C | Observational | Phase 1 | 43% | ... |
| 1004 | Drug D | Observational | Phase 2 | 53% | ... |
| 1005 | Drug E | Interventional | Phase 2 | 66% | ... |
| 1006 | Drug F | Observational | Phase 2 | 58% | ... |
| 1005 | Ingredient X | - | - | - | ... | dB2 record table:

| Record ID | Record Title | Type | Trial Stage | Success rate | ... |
|---|---|---|---|---|---|
| 2001 | Drug P | Interventional | Phase 2 | 48% | ... |
| 2002 | Drug Q | Expanded acc | Phase 3 | 82% | ... |
| 2003 | Drug R | Interventional | Phase 2 | 63% | ... |
| 2004 | Ingredient Z | - | - | - | ... |

Fig. 2

Predetermined facet linking table: 500

| Facet ID 501 | Data Src ID 502 | SR Prop ID 503 |
|---|---|---|
| Type | dB1 | Type |
| Type | dB2 | Type |
| Phase | dB1 | Phase |
| Success Rate | dB2 | Success Rate |
| Success Rate | ... | ... |

510

Query-specific additional facet link:

| Facet ID 501 | Data Src ID 502 | SR Prop ID 503 |
|---|---|---|
| Phase | dB2 | Trial stage |

Modified predetermined
facet linking table:

| Facet ID | Data Src | SR Prop |
|---|---|---|
| Type | dB1 | Type |
| Type | dB2 | Type |
| Phase | dB1 | Phase |
| Success Rate | dB2 | Success Rate |
| Success Rate | dB2 | Success Rate |
| Phase | | Trial stage |
| ... | ... | ... |

Fig. 8

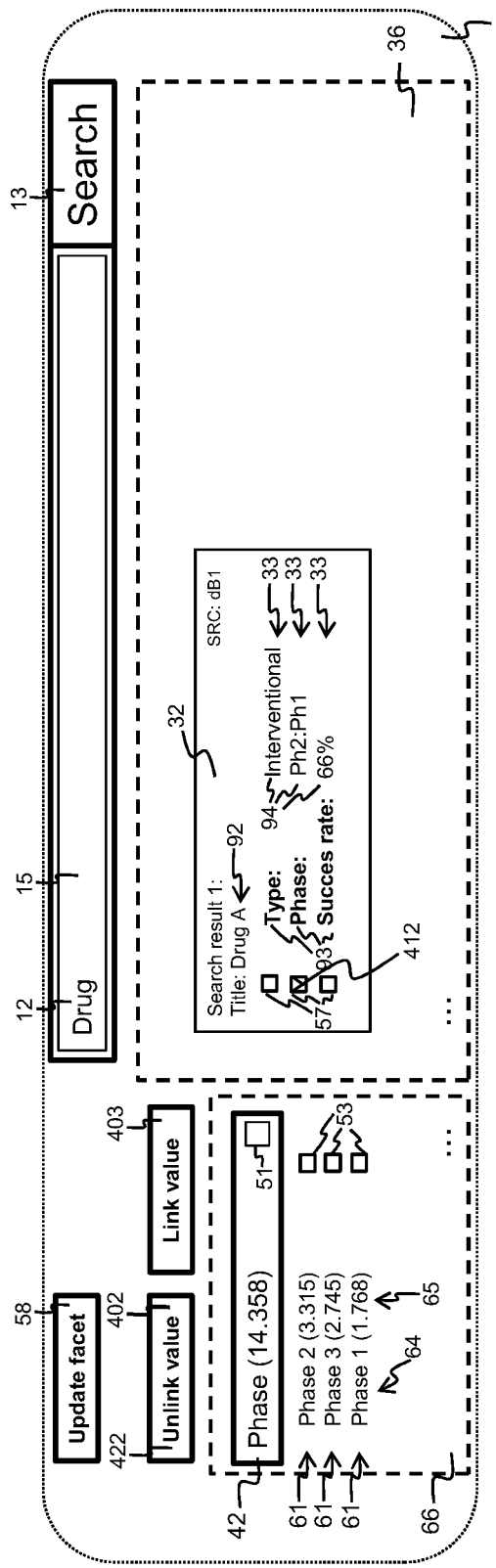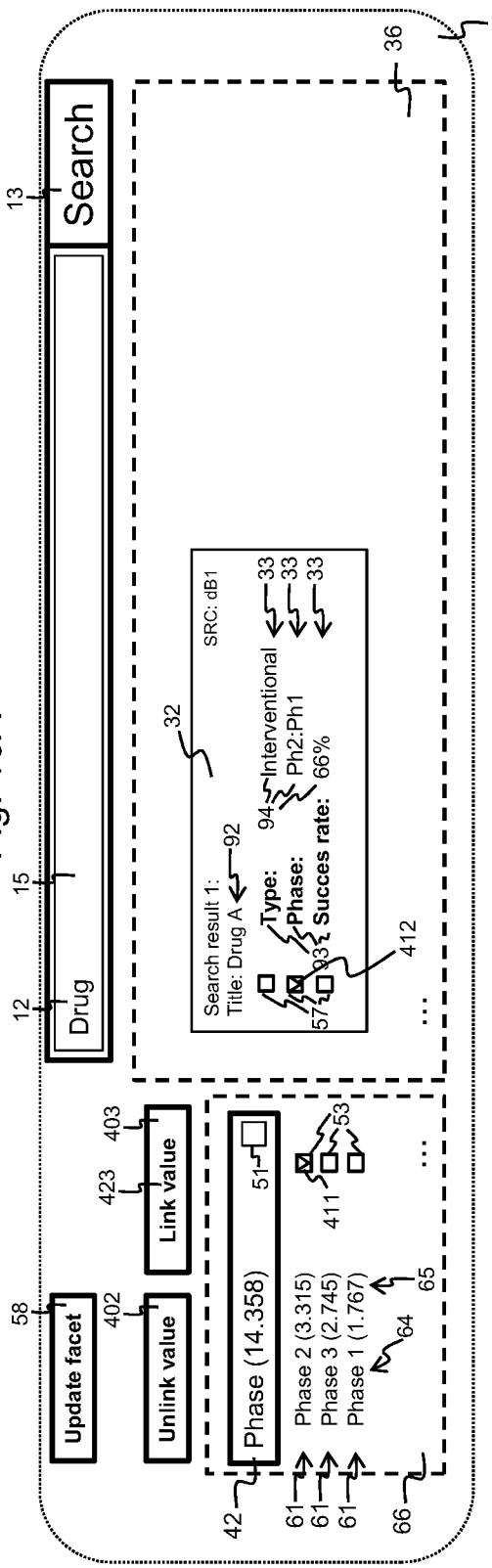

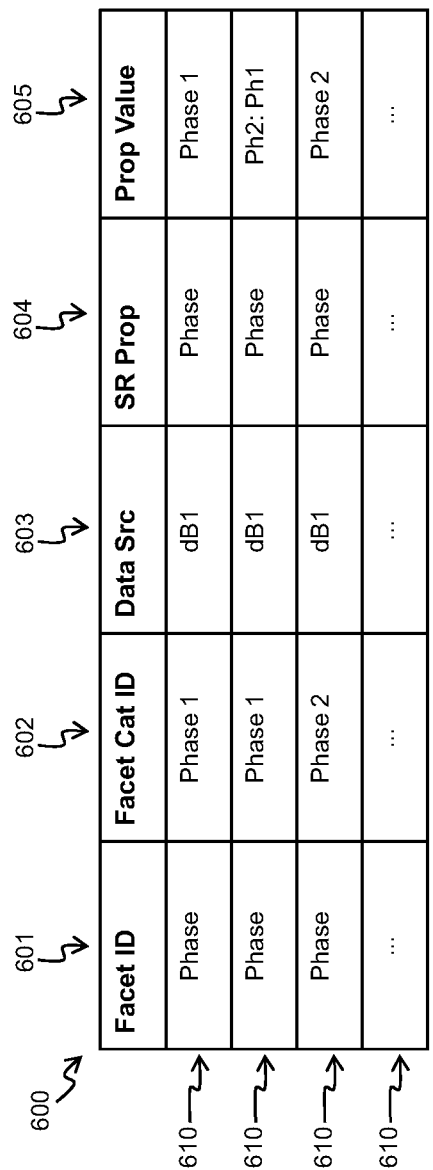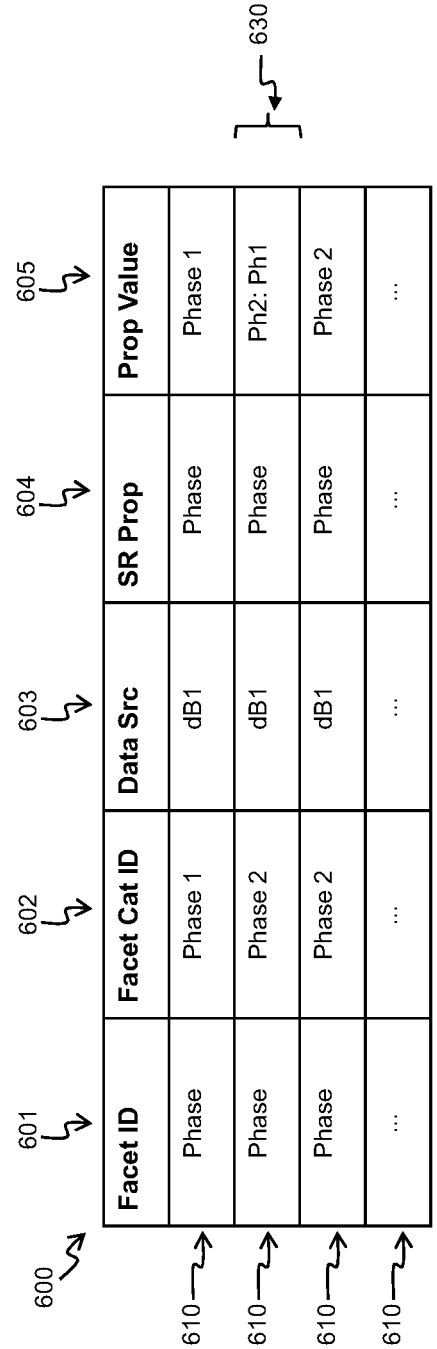

DATA PROCESSING SYSTEM FOR CURATING SEARCH RESULT FACETS

FIELD OF THE INVENTION

The present invention generally relates to a data processing system for retrieving faceted search results. The invention more specifically relates to a data processing system for updating or curating search result facets and corresponding facet categories.

BACKGROUND OF THE INVENTION

Faceted search, also called faceted navigation or faceted browsing, is a technique for accessing information organized according to a faceted classification system. In a context of search systems accessing a vast amount of information, producing a large number of search results such a faceted classification system allows users to explore and refine the search results by applying suitable filters. Such a faceted classification system enables the possibility to classify search results dynamically, rather than in a single, pre-determined, taxonomic order. Facets correspond to properties of the search results. These facets can for example be determined in function of pre-existing fields in a database, that form properties of the search results. Such facets could be determined in function of database fields, such as for example the author, description, language, dates, prices, technical features, etc. This allows for example to refine search results resulting from a query "digital camera" on a database storing items sold through an online shop to be refined by using the following facets, "price", "resolution", "brand", etc. Alternatively or additionally facets could also be determined in function of analysis of the text content related to a search result for example by using entity extraction techniques. Faceted search in this way enables users to navigate a multi-dimensional information space by combining text search with a progressive adaptation of choices in each dimension by means of these facets. An example of a known computer implemented process for searching a single database by means of predetermined facets representing fields of this database is for example known from US2008/086451.

A computer system for performing faceted classification synthesis is for example known from US20070118542. Herein concepts are represented by concept definitions defined in accordance with a faceted data set comprising facets, facet attributes, and facet attribute hierarchies are related. The computer system is configured for expressing dimensional concept relationships between the concept definitions, wherein two concept definitions are determined to be related in a particular dimensional concept relationship by examining whether at least one of explicit relationships and implicit relationships exist in the faceted data set between the respective facet attributes of the two concept definitions.

Such computer system allows for updating the concept definitions. For example, the embodiment corresponding to FIG. 27 of US20070118542 discloses a user interface wherein an automatically generated dimensional taxonomy is presented to the user. The user interface allows the user to manually change the location of nodes in the classification structure and thereby to reorganize the hierarchy.

However, in the context of a search system covering a plurality of large scale databases, in which new databases are added and removed over time and each of these large scale databases themselves evolving over time, such prior art systems present several difficulties. Such search systems are for example in use in the context of pharmaceutical companies in which researchers make use of information contained in large number of databases, for example freely accessible external databases, external databases provided by commercial providers, in-company databases, etc. providing data about for example genes, proteins, clinical data, patient histories, clinical trials, molecules, etc.

Every time a new database is made accessible to the search system or every time the setup of an existing database is changed, extensive programming and configuration is necessary in order to automatically generate and/or manually update relevant search result facets in a correct way. Furthermore, facet generation and modification for such complex data is not an easy task for a programmer to perform. The programmer typically will not have the necessary experience to understand domain-specific hierarchies and/or dependencies in e.g. clinical data, molecule data, etc. Errors or omissions often only become apparent when users execute specific queries. However, these users lack knowledge or tools necessary to make adjustments.

There still exists a need to improve efficiency and flexibility in generating and/or updating search result facets in view of a faceted search system which is connected to a developing database system.

SUMMARY OF THE INVENTION

According to a first aspect of the invention there is provided a data processing system for updating search result facets, the data processing system comprising:
an input module configured to receive a search query;
a plurality of data sources comprising at least a first data source and a second data source;
a retrieval module connected to the input module and the data sources and configured to:
  receive from a user via the input module the search query; and
  retrieve a search result list comprising a plurality of first search results from the first data source and a plurality of second search results from the second data source in function of the search query, the first and second search results respectively comprising a plurality of first and second search result properties, each comprising a search result property identifier and a search result property value;
a facet module connected to the retrieval module, the facet module comprising a facet linking module configured to:
  provide a search result facet list comprising one or more search result facets and one or more search result facet categories per search result facet, wherein a search result facet corresponds to a subset of search results of the search result list, wherein a search result property identifier of each of the search results is linked with the search result facet via one of a set of predetermined facet links, wherein a search result facet category of the search result facet corresponds to one or more search results of the subset and wherein the search result property value of the one or more search results belongs to the facet category, and wherein the set of predetermined facet links comprises at least one predetermined first facet link defining a link between a search result facet and a search result property identifier of a first search result property,
wherein when the set does not comprise a predetermined second facet link defining a link between the search result facet and a search result property identifier of a non-linked second search result property, the data processing system is further configured to:
- determine a selected second search result property in view of the non-linked second search result property;
- determine a selected search result facet in view of the search result facet;
- upon reception of a facet linking command update the one or more facet categories of the selected search result facet in view of the search result property values of the selected second search result property.

In this way, there is provided the possibility for a user to curate a search result facet while carrying out a search query. The user can link a search result facet with a non-linked search result property. For example, a facet corresponding to a first search result property 'price' can be updated by a user during query time, with a second not yet linked search result property 'cost' of search results from e.g. a recently added or new database. Hereby, the user can easily update facet categories while carrying out the search query.

The terms "updating" or "curating" in underlying disclosure should be understood as a modification or reorganizing of data or content. It is self-evident that the terms "updating" or "curating" are to be interpreted interchangeably.

According to a preferred embodiment the data processing system further comprises a search result property selection module for determining a selected second search result property, which module is connected to the retrieval module and facet module and is configured to:
- receive from the user via the input module a property selection of a second search result property of a second search result of the search result list, wherein the second search result property corresponds to the selected second search result property.

According to a preferred embodiment the data processing system further comprises a search result facet selection module for determining a selected search result facet, which module is connected to the facet module and configured to:
- receive from the user via the input module a facet selection of a search result facet of the search result facet list, wherein the search result facet corresponds to the selected search result facet.

According to a more preferred embodiment the facet module further comprises a facet updating module configured to:
- receive from the user via the input module a facet linking command corresponding to the property selection and the facet selection.

According to an embodiment the facet module is further configured to update the one or more facet categories of the selected search result facet by providing an additional facet link defining a link between the selected search result facet and the search result property identifier of the selected second search result property.

According to a preferred embodiment the additional facet link is query-specific.

There is no need to change the system directly, as the facet in first instance is modified specifically for the search query, and thereby for the user. Updating facets directly on system-level would require extensive consultation of end users and/or would result in a possible sub-optimal user experience, as other users maybe do not prefer the additional property linked to the facet.

According to an embodiment the set of predetermined facet links is updated by adding an additional predetermined facet link to the set, the additional predetermined facet link defining a link between the selected search result facet and the search result property identifier of the selected second search result property.

Hereby, the data processing system allows to update the predetermined search result facet and corresponding facet categories in view of the selected second search result property, on system-level. Based on the update of the search result facet and facet categories by the user, whom carries out the search query, the data processing system will be accordingly updated for other users connected to the system.

According to a preferred embodiment the set of predetermined facet links is updated by adding the additional predetermined facet link to the set, when the number of facet linking commands corresponding to the property selection and the facet selection and received by the facet updating module exceeds a predetermined threshold.

The predetermined threshold allows for the updating of search result facets which were updated a certain number of times by one or more users in the same way. Hereby, quality of search result facets and corresponding facet categories will be improved, leading to a more flexible data processing system in view of frequently added or removed databases over time.

According to a preferred embodiment the set of predetermined facet links is updated by aggregating additional predetermined facet links to the set for a plurality of users of the data processing system.

A plurality of users carrying out search queries and thereby updating search result facets and facet categories, allows for a rapid and dynamic optimization of the data processing system.

According to an embodiment the retrieval module is further configured to:
- receive from a user via the input module a facet category selection of an updated facet category of the search result facet list provided by the facet module;
- receive from the user via the input module a faceted searching command corresponding to the facet category selection;
- retrieve a faceted search result list comprising a plurality of search results from the plurality of data sources in function of the search query and the selected updated facet category.

Hereby, it allows for a user to update a search result facet and facet categories and to carry out a faceted search based on the updated facet and facet categories while the user is searching for the relevant information.

According to an embodiment, the data processing system is further configured to:
- determine a selected first facet category of a search result facet;
- determine a selected second facet category of the search result facet;
- upon reception of a facet category merging command, update the selected first facet category in view of the search result property values of the selected second facet category.

According to an embodiment, the data processing system is further configured to:
- determine a selected search result property value of a facet category of a search result facet;
- upon reception of a property value unlinking command, unlink the selected search result property value from the facet category.

According to an embodiment, the data processing system is further configured to:
- determine a selected search result property value;

determine a selected facet category;
upon reception of a property value linking command, link the selected search result property value to the selected facet category.

According to an embodiment, the data processing system is further configured to:
determine a selected search result property value of a first facet category of a search result facet;
determine a selected second facet category of the search result facet;
upon reception of a property value moving command, unlink the selected search result property value from the first facet category and link the selected search result property value to the selected second facet category.

According to a second aspect of the invention there is provided a computer implemented method for updating search result facets comprising the steps of:
receiving a search query from a user;
retrieving a search result list comprising a plurality of first search results from a first data source and a plurality of second search results from a second data source in function of the search query, the first and second search results respectively comprising a plurality of first and second search result properties, each comprising a search result property identifier and a search result property value;
providing a search result facet list comprising one or more search result facets and one or more search result facet categories per search result facet, wherein a search result facet corresponds to a subset of search results of the search result list, wherein a search result property identifier of each of the search results is linked with the search result facet via one of a set of predetermined facet links, wherein a search result facet category of the search result facet corresponds to one or more search results of the subset and wherein the search result property value of the one or more search results belongs to the facet category, and wherein the set of predetermined facet links comprises at least one predetermined first facet link defining a link between a search result facet and a search result property identifier of a first search result property;
wherein when the set does not comprise a predetermined second facet link defining a link between the search result facet and a search result property identifier of a non-linked second search result property:
determining a selected second search result property in view of the non-linked second search result property;
determining a selected search result facet in view of the search result facet;
upon reception of a facet linking command updating the one or more facet categories of the selected search result facet in view of the search result property values of the selected second search result property.

According to an embodiment, the method further comprises:
updating one or more facet categories of the selected search result facet by providing an additional facet link defining a link between the selected search result facet and the search result property identifier of the selected second search result property.

According to an embodiment, the method further comprises:
receiving from a user a facet category selection of an updated facet category of the search result facet list;
receiving from the user a faceted searching command corresponding to the facet category selection;
retrieving a faceted search result list comprising a plurality of search results from the plurality of data sources in function of the search query and the selected updated facet category.

According to an embodiment, the method further comprises:
a user selecting a first facet category of a search result facet;
the user selecting a second facet category of the search result facet;
the user providing a facet category merging command for the first and second facet categories;
merging the first facet category with the second facet category by updating the first facet category in view of the search result property values of the second facet category.

According to a third aspect of the invention there is provided a computer readable medium comprising computer-executable instructions, which when executed by a data processing system, perform the method according to the second aspect of the invention.

BRIEF DESCRIPTION OF THE DRAWINGS

FIG. 2 illustrates an exemplary number of data records stored in a first and a second database connected to the data processing system of FIG. 1;

FIG. 3 illustrates an exemplary number of predetermined search result facet links for the facet linking module of the data processing system of FIG. 1;

FIG. 8 illustrates a modified set of predetermined search result facet links for the facet linking module of the data processing system of FIG. 1.

FIGS. 12(A) and 12(B) illustrate a facet category linking table for the data processing system corresponding to FIGS. 10(A)-11.

DETAILED DESCRIPTION OF EMBODIMENT(S)

Figure 1:
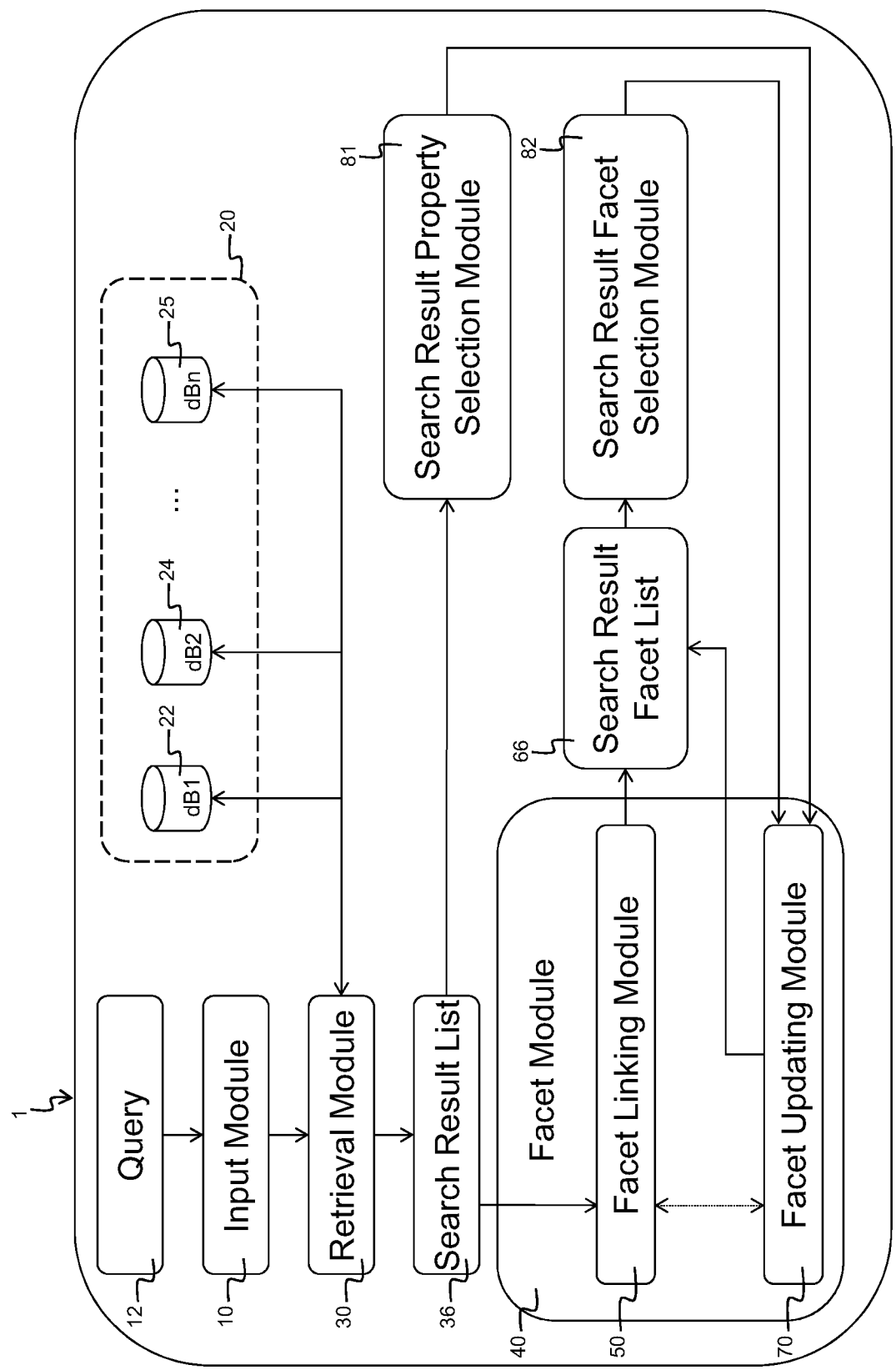
FIG. 1 schematically illustrates a data processing system for updating search result facets.

An embodiment of a data processing system 1 for updating search result facets also referred to as a faceted search system is shown in FIG. 1. It comprises an input module 10 by which the system 1 can receive a search query 12 from a user. Such an input module 10 could for example receive a search query 12 from a suitable input box 15 on a user interface 80, such as for example shown in FIGS. 5-7. The retrieval module 30 that is connected to the input module 10 receives this search query 12 from the input module 10. The retrieval module 30 will subsequently retrieve a plurality of search results based on this query 12 and provide them to the user in a search result list 36. These search results could for example be suitable results from a query based on the search query 12 performed on the plurality of databases 20, which comprises the first database 22, the second database 24 and possible other databases 25. The search query 12 could for example relate to a specific disease "Artherosclerosis" and a type of publications "Assay". The retrieval module 30 will translate these keywords to suitable instructions for retrieval of search results in a freely available external database, a commercial external database, an in-company database, etc.

These databases or data sources contain data records with information. FIG. 2 shows two simplified tables 220, 240 illustrating a number of stored data records for respectively the first database 22 and the second database 24. The table 220 for the first database 22 contains a list of data records 226. Each data record 226 comprises a data record value 229 per corresponding data record field. Possible data record fields are a data record identifier 221, a data record title 222 and data record properties 'Type' 223, 'Phase' 224 and 'Succes Rate' 225. The second table 240 for the second database 24 contains a list of data records 246. Each data record 246 also comprises a record value 249 per corresponding record data field, such as the record identifier 241, the data record title 242 and the data record properties 'Type' 243, 'Phase' 244 and 'Succes Rate' 245.

According to the exemplary embodiment, a search result list 36 will be returned comprising a plurality of first search results 32 from the first data source 22 and a plurality of second search results 34 from the second data source 24. A first search result 32 corresponds to a data record 226 of the first database 22. The first search result 32 comprises one or more first search result properties 33, wherein a first search result property 33 comprises a search result property identifier 93 and a search result property value 94. The search result property identifier 93 corresponds to a data record property 223-225 of the data record 226. The search result property value 94 for said first search result property 33 corresponds to the data record value 229 of the data record property 223-225 for said corresponding data record 226.

For example, a search result 32 corresponds to a data record 226 in the first database 22 with record identifier '1001'. The search result property identifier 93 for the search result property 33 corresponds to the data record property 223 'Type' (see FIG. 2). The search result property value 94 for the same search result property 33 corresponds to the data record value 229 'Interventional'.

A second search result 34 corresponds to a data record 246 of the second database 24. The second search result 34 comprises one or more second search result properties 35, wherein a second search result property 35 comprises a search result property identifier 93 and a search result property value 94. The search result property identifier 93 corresponds to a data record property 243-245 of the data record 246. The search result property value 94 for said second search result property 35 corresponds to the data record value 249 of the data record property 243 for said corresponding data record 246.

The search result property values 94 qualify as a search result facet 42, this means they allow for further filtering or faceted navigation in the retrieved search results 32,34. Examples of properties that could qualify as a search result facet 42 are for example publication dates, dates of phases of clinical trials, phases of clinical trials, publication types, names of authors, names of pharmaceutical companies, target diseases, type of test subject, therapeutic area, clinical trial success rate, etc. Each of these facets allow for further filtering, for example by limiting the range of publication dates or to provide pointers to additional search results, for example by providing links to other search results for the top 5 authors, top 10 related target diseases related to search results of the current query. It is clear that search result properties such as unique identifiers, title, abstract, etc. as such would not qualify as a search result facet 42.

The data processing system 1 is provided with a facet module 40 that is connected to the retrieval module 30. The facet module 40 comprises a facet linking module 50 which is configured to provide a search result facet list 66 based on said search result list 36 provided by the retrieval module 30 and based on one or more predetermined facet links 510.

The search result facet list 66 comprises at least one search result facet 42, which search result facet 42 depends on at least one predetermined facet link 510, wherein the predetermined facet link 510 defines a link between a search result facet identifier 501 corresponding to the search result facet 42 and a search result property identifier 503 corresponding to a first search result property 33 of a retrieved search result 32 of the search result list 36.

FIG. 3 illustrates an example of a set 500 of predetermined facet links 510, represented by a simplified table 500. Each facet link 510 is represented by a facet link identifier 501, a data source identifier 502 and a search result property identifier 503. The facet link identifier 501 corresponds to a possible search result facet 42 for the search result facet list 66. A search result property identifier 503 of a facet link 510 corresponds to a possible search result property identifier 93 for a first search result property 33 or second search result property 35. Each search result property identifier 503 is also linked to a data source 22,24 which is represented by the data source identifier 502.

Based on the set 500 of predetermined facet links 510, the facet linking module 50 will provide a search result facet list 66 with one or more search result facets 42. Each search result facet 42 corresponds to a subset of the search results for the retrieved search result list 36, wherein a search result property identifier 93 of each of said search results is linked with the facet identifier 501 of said search result facet 42.

Further, the facet search result list 66 comprises one or more search result facet categories 61 per corresponding search result facet 42. A facet category 61 of a search result facet 42 corresponds to one or more retrieved search results 32,34, wherein the search result property value 94 of the retrieved search result 32,34 belongs to said facet category 61. A facet category can for instance be a range of values, e.g. 20%-30%, wherein a value of 26% belongs to said facet category 61. Also, a facet category 61 can be a specific value, wherein a search result property value 94 equalling said specific value thereby belongs to said search result facet category 61. Search result facets values can have differing data types, as publication date or other time based values. A search result value can also correspond to a 'person' datatype, such as authors, inventor, speaker, etc. Other suitable data types could be available for gene sequences, molecules, diseases, companies, geographic information, target disease, etc.

The system 1 also comprises a search result property selection module 81 connected to the retrieval module 30 and the facet module 70 (see FIG. 1). This module 81 is configured to select by a user a search result property 33,35 of a search result 32,34 of the search result list 36, wherein this property selection 52 is provided to the facet module 70.

The system 1 also comprises a search result facet selection module 82 connected to the facet module 70. This module 82 is configured to let a user select a search result facet 42 of the search result facet list 66, wherein this search result facet selection 54 is provided to the facet module 70.

The facet linking module 50 further comprises a facet updating module 70, which is configured to update facet categories 61 of the selected search result facet 42 in view of the search result property values 94 of the selected search result property 35. This is done by providing a query-specific additional facet link 530 (see also FIG. 3), defining a link between the search result facet identifier 501 corresponding to the selected search result facet 42 and the search result property identifier 503 corresponding to the search result property identifier 93 of the selected search result property 35.

Figure 4:
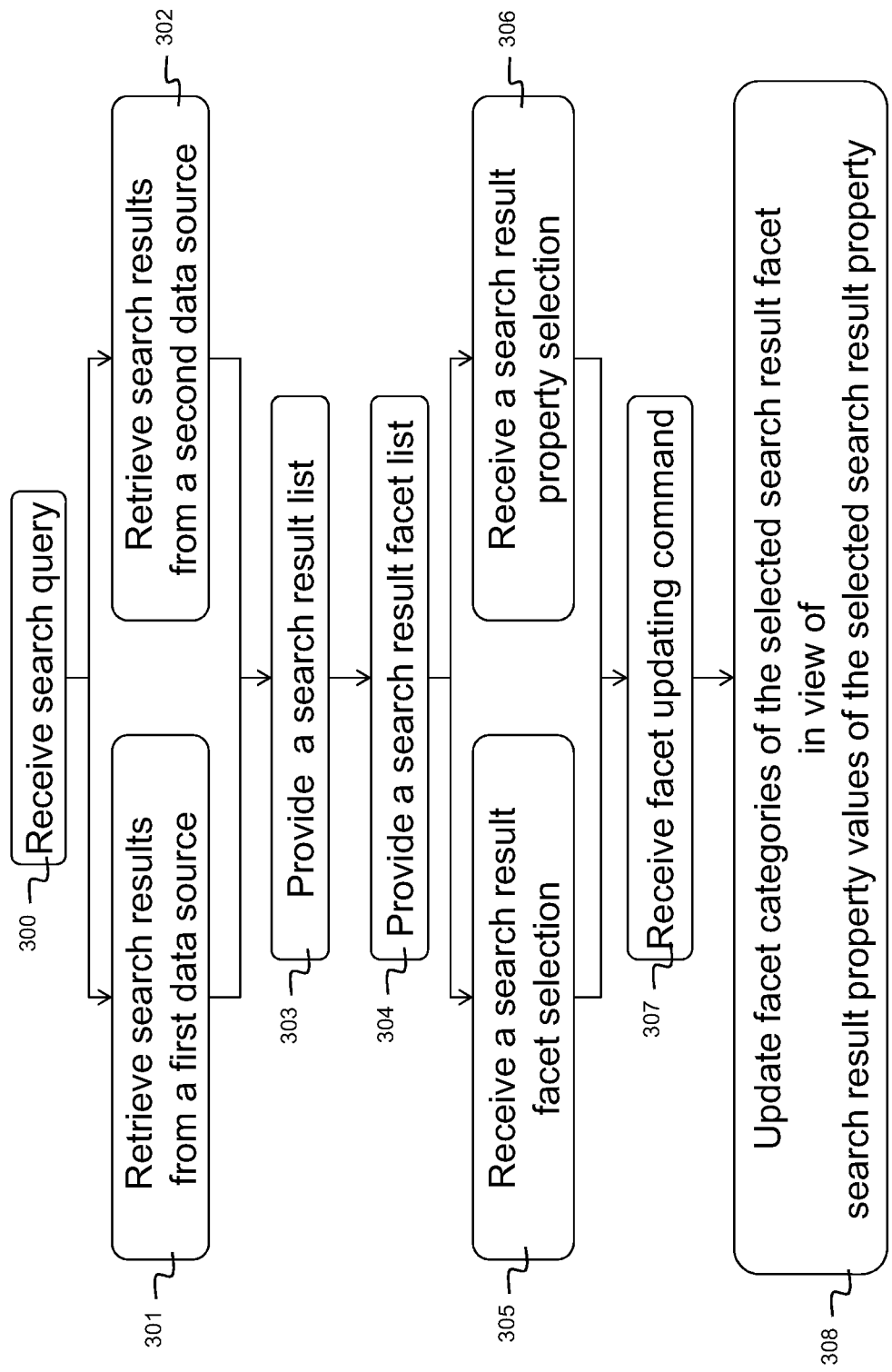
FIG. 4 illustrates a method for operating a data processing system according to an embodiment of the invention.

In general the data processing system 1 is operated by means of a computer implemented method for modifying search result facets, performing the steps shown in FIG. 4. Such a computer implemented method could be provided as computer-executable instructions on a computer readable medium, which when executed by a data processing system, perform this method.

Initially, a user gives in a search query 12, which is received by the retrieval module 30 in step 300. Subsequently, search results 32 are retrieved from the first data source 22 in step 301, together with the retrieval of search results 34 from the second data source 24 in step 302. The retrieval module 30 provides in step 303 a search result list 36, comprising said retrieved search results 32,34. Based on the retrieved search result list 36 and based on one or more predetermined facet links 510, the facet linking module 50 of the facet module 40 provides a search result facet list 66 in step 304. The search result facet list 66 comprises at least one search result facet 42 with at least one corresponding facet category 61.

The user can select, e.g. via a user interface 80, a search result property 35 of a search result 34 of the search result list 36 in step 305, wherein this property selection 52 is provided to the facet updating module 70 of the facet module 40.

The user can also select, e.g. via a user interface 80, a search result facet 42 of the search result facet list 66 in step 306, wherein this facet selection 54 is provided to the facet updating module 70 of the facet module 40.

After that, the user provides a facet updating command 56 based on the property selection 52 and the facet selection 54 via the input module 10 in step 307 to the facet updating module 70.

As a result, upon reception of the facet updating command 56 by the facet updating module 70, it will provide a query-specific facet category update for the selected search result facet 42 in the search result facet list 66.

This means that the facet updating module 70 will provide an updated search result facet list 66, wherein the facet categories 61 of the selected search result facet 42 are updated in view of the search result property values 94 of the selected search result property 35.

Figure 5:
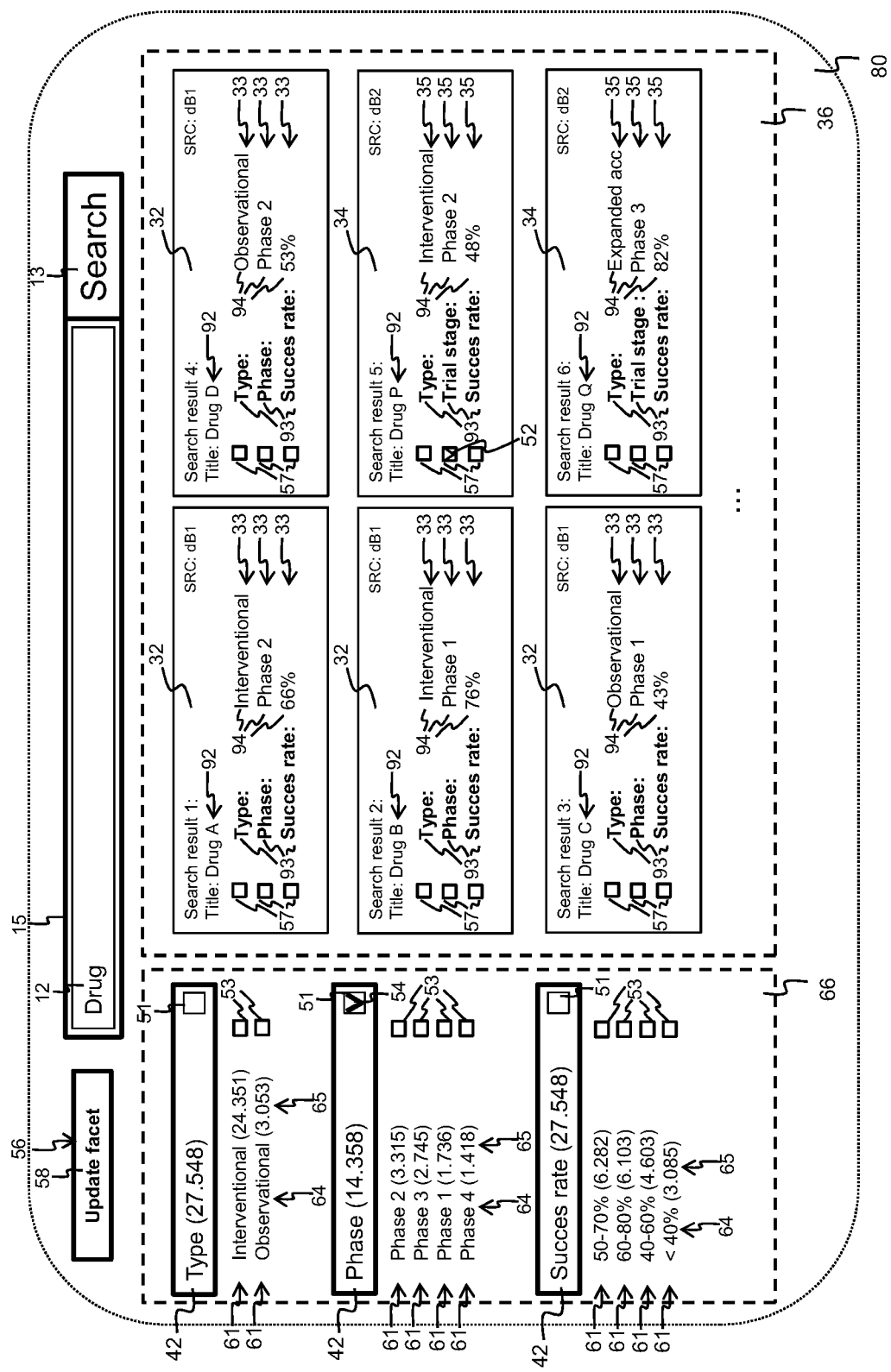
FIGS. 5-7 illustrate an exemplary user interface for the data processing system of FIG. 1.
Figure 6:
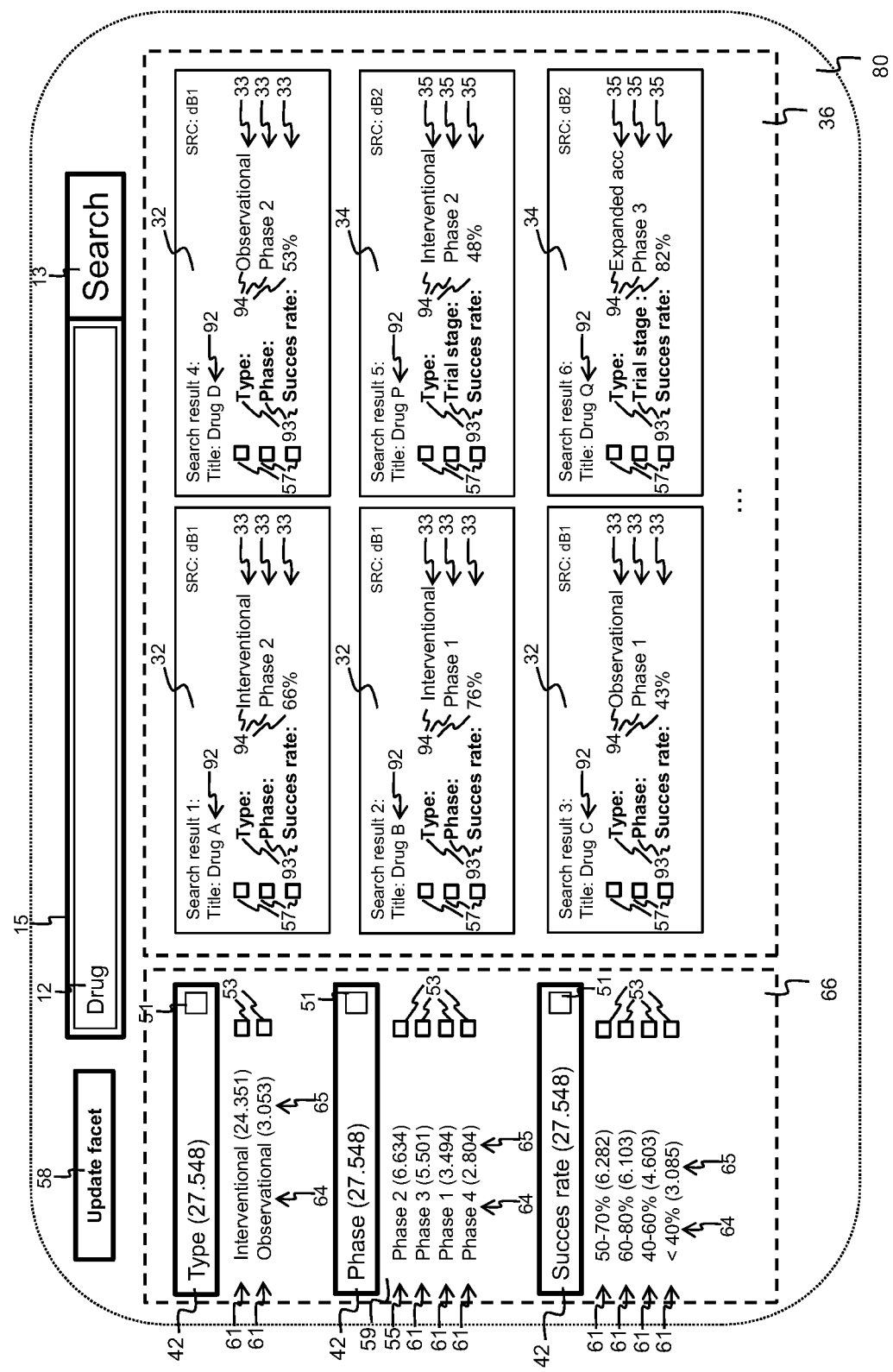
Figure 7:
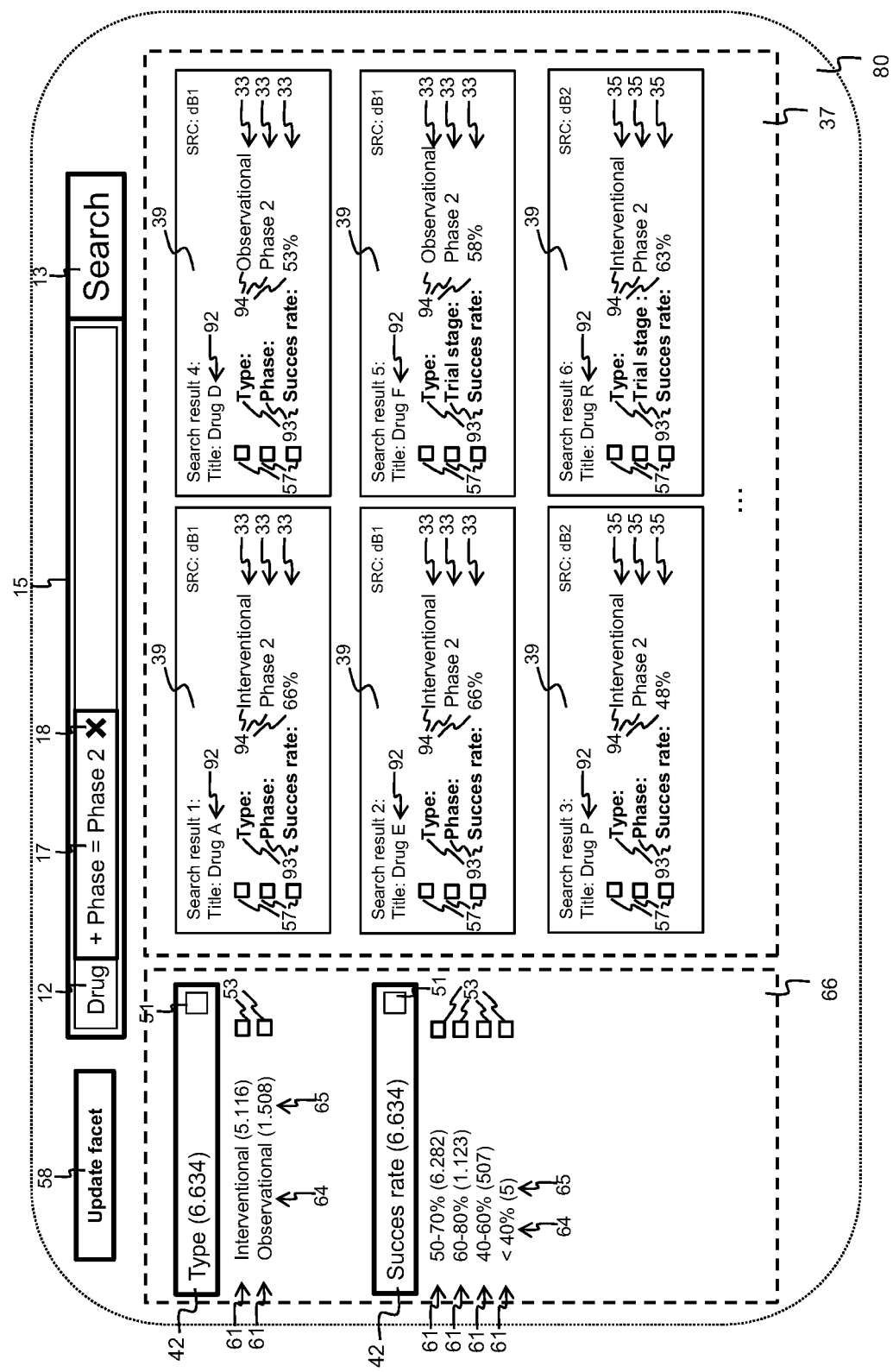

As an example, the user interface 80 in FIGS. 5-7 illustrates an embodiment for the method steps shown in FIG. 4.

A user gives in the search query 12 "Drug" into the input box 15 and presses the search button 13. The retrieval module 30 will retrieve according search results from the plurality 20 of data sources. Retrieved search results are for example based on a text search of "drug" within the record titles 222,242 is of the data records 226,246 stored on the plurality 20 of data sources. A search result list 36 is provided, wherein six search results 32,34 are shown on the user interface 80. It is clear that the amount of listed search results can be different, and can for example be a predetermined or user-adjustable value. In this example, the first four search results 32 were retrieved from the first database 22. A first search result 32 contains a search result title 92 and first search result properties 33, with search result property identifiers 93, i.e. 'type', 'phase' and 'success rate' and corresponding search result property values 94. A second search result 34 contains a search result title 92 and second search result properties 35, with search result property identifiers 93, i.e. 'type', 'trial stage' and 'success rate' and corresponding search result property values 94. Each search result property value 94 is provided with an accompanying check box 57.

Further, the user interface 80 provides a search result facet list 66 with search result facets 42 'Type', 'Phase' and 'Success rate', shown together with the amount of retrieved search results from the plurality 20 of data sources. The search result facets 42 can be selected by the accompanying check boxes 51. Together with the presented search result facets 42, the search result facet list 66 comprises search result facet categories 61, which are listed per search result facet 42 with corresponding amount 65 of retrieved search results belonging to said search result facet category 61.

When the user interprets the shown search result list 36, he may notice that for example the amount of search results for the facet 42 'Phase' is lower than expected. This could be explained as the facet 42 'Phase' and thereby the corresponding facet categories 61 are not linked to the property 35 'trial stage', which relates to the same property. The facet 42 'Phase' depends on the search result property identifier 'Phase' (see FIG. 3), but no link is provided to the search property identifier 93 'Succes Rate'.

For this reason, the user checks the checkbox 51 of the search result facet 'Phase' 42, and hereby makes the facet selection 54. The user also selects the checkbox 57 of the second search result property 35 with identifier 93 'Trial stage' of the fifth search result 34 from the search result list 36, and hereby provides the property selection 52. By clicking the facet updating button 58, the user provides a facet updating command 56 based on the property selection 52 and the facet selection 54 to the facet updating module 70.

As a consequence, an additional query-specific facet link 520 will be created for the selected search result facet 42 'Phase' (see also FIG. 3). The additional facet link 520 defines the link between the selected search result facet 42 and the search result property identifier 'Trial Stage' 93 of the selected search result property 35. The search result facet 42 'Phase' and corresponding search result facet categories 61 will be updated and now depend on this additional link 520.

As a result, the user interface 80 is updated as shown in FIG. 6. The amount of retrieved search results 34 corresponding to the query-specific updated facet 'Phase' is increased with the amount of search results comprising the search result property identifier 93 'Trial stage'. The amount of retrieved search results 34 corresponding to the corresponding query-specific updated facet categories 61 are increased with the amount of search results comprising the corresponding search result property values 94.

The facet 42 and facet categories 61 are updated query-specific, which means during the carrying out of the search query process by the user.

In this way, when the initial predetermined search result facet links 510 that are set up for example when a new database is added to the faceted search system 1, are sub-optimal, based on user feedback the system will temporarily adapt during use in order to attain a more optimized setup for searching records.

Further, the user can decide to filter the retrieved search results by the facet 'Phase' with facet category 61 'Phase 2' by the facet category selection 55, e.g. by means of clicking the area 59.

FIG. 7 shows the user interface 80 for the corresponding faceted search query based on the search query 12 'Drug' and the selected search result facet 42 'Phase' and corresponding search result facet category 61 'Phase 2' shown by the section 17. The x-symbol allows for removing the selected search result facet category 61 from the search query again.

Six corresponding search results 39 are listed in the faceted search list 37. The search result property identifiers 93 'phase' and 'trial stage', both contain the facet value 'Phase 2' as selected by the user for this faceted search. Further, other search result facets 42 'Type' and 'Success rate' are shown with corresponding selectable search result facet categories 61, for further possible filtering of the search results 39 in the list 37.

In a further embodiment of the invention, the set of predetermined facet links 510 for the data processing system 1 can be updated, when a certain number of times the same facet linking command 56 has been received by the facet linking module 50. When for example the facet linking command 56 corresponding to a certain property selection 52 and a certain facet selection 54 has been requested a minimum of n times by one or more users, the system will update the set 500 of predetermined facet links 510 by defining an additional search result facet link 530 for the search result property identifier 93 'trial stage' and the search result facet identifier 93 'Phase'. Herein the number n corresponds to a predetermined threshold, e.g. 1, 2, 3, 4, 5, etc. This greatly reduces overhead and flexibility when coping with the introduction of new data sources or changes to existing data sources. Users carrying out search queries can thereby help updating and optimizing the system 1.

In case for the user interface 80 in FIG. 3, the facet linking command 56 corresponding to the search result property value 94 for the search result property identifier 93 'trial stage' and the search result facet 42 'Phase' is requested to the facet linking module 50 for the fifth time, and e.g. the predetermined threshold equals five, then in case of this further embodiment, the set 500 of predetermined facet links 510 is updated as shown in FIG. 8.

The set 500 of predetermined facet links 510 now has an additional facet link 530 referring to the search result property identifier 93 'Trial stage'. This means the system 1 is updated with this search result property identifier 93, so future search result facets 42 and corresponding search result facet categories 61 will also directly depend on the added property identifier 93 'Trial stage', together with the already linked search result property identifier 93 'Stage'.

Figure 9A:
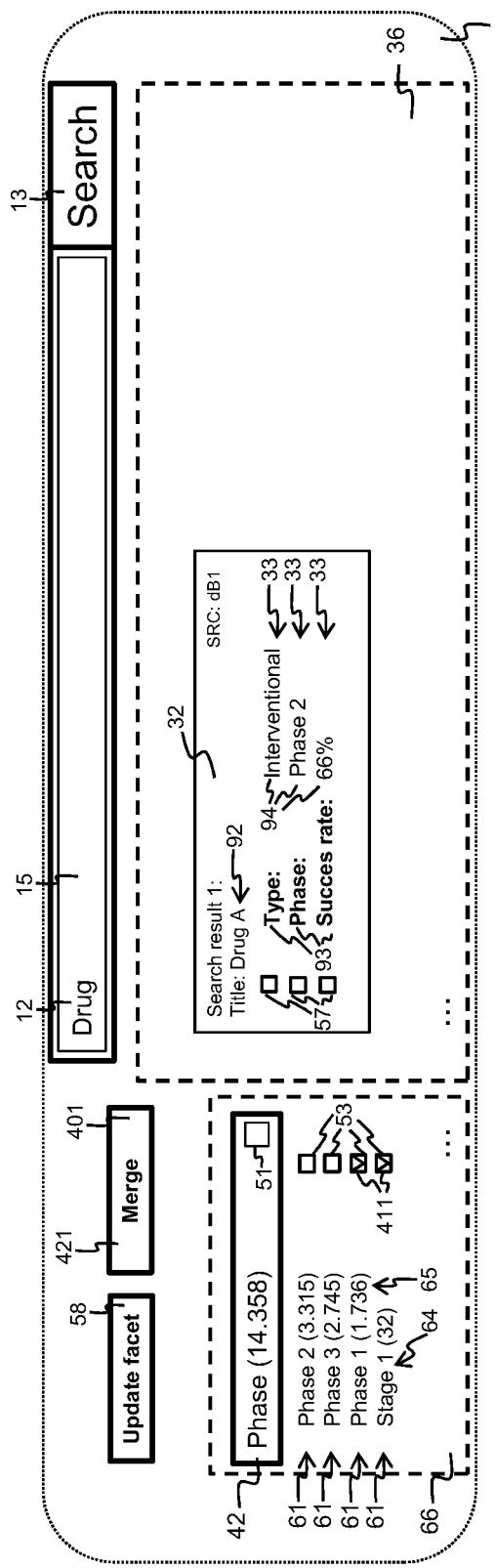
FIGS. 9(A)-11 illustrate further embodiments of an exemplary user interface for the data processing system of FIG. 1.
Figure 9B:
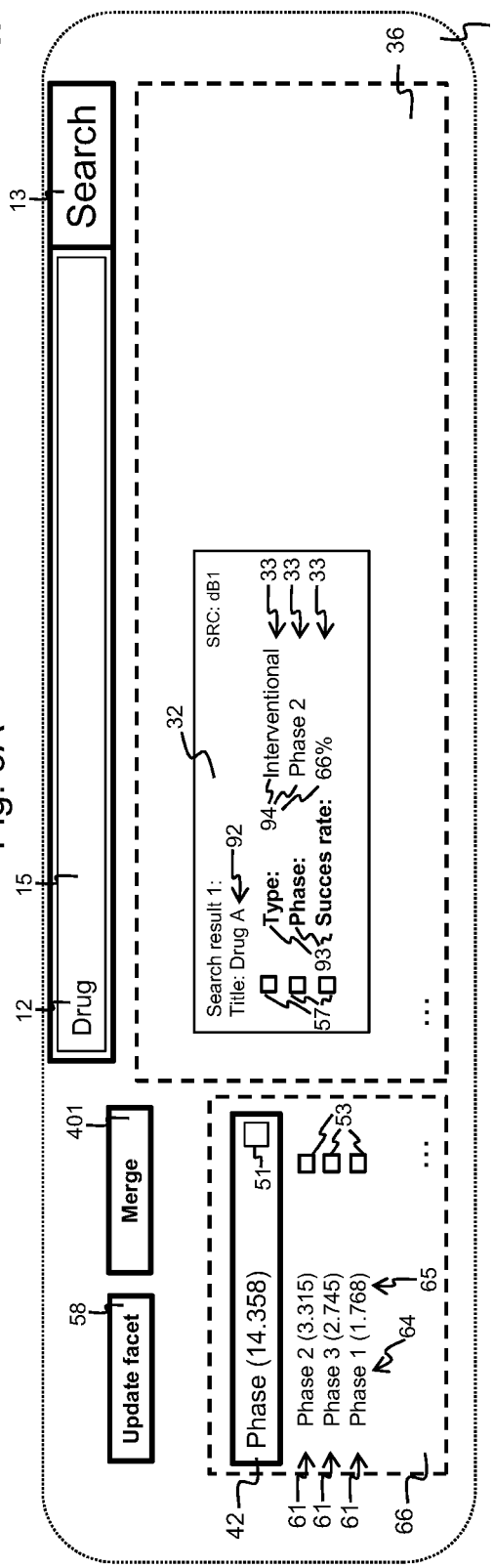

FIGS. 9A and 9B illustrate a further embodiment of the user interface 80 as illustrated in FIGS. 5-7. The user interface 80 is further provided with a facet category merging button 401. Typically with developing database systems, facet structuring often needs reorganization. For example, two different facet categories 61 of a search result facet 42, are meant to categorize in the same way. For example, 'Phase 1' and 'Stage 1' correspond to the same pharmaceutical phase for the facet 42 'Phase'. Thereto, a user can make a selection 411 of the checkbox 53 for the facet category 61 'Phase 1' together with a selection 411 of the checkbox 53 corresponding to the facet category 61 'Stage 1' and subsequently can press the facet category merging button 401, therewith giving a facet category merging command 421 to the data processing system 1 (See FIG. 9A). As a result, the first selected facet category 61 'Phase 1' is updated with the search result property values 94 corresponding to the other selected facet category 61 'Stage 1' (See FIG. 9B). The redundant facet category 61 'Stage 1' is removed from the search result facet list 66 and the amount 65 of retrieved search results belonging to the search result facet category 'Phase 1' is updated accordingly (i.e. increased).

Figure 10C:
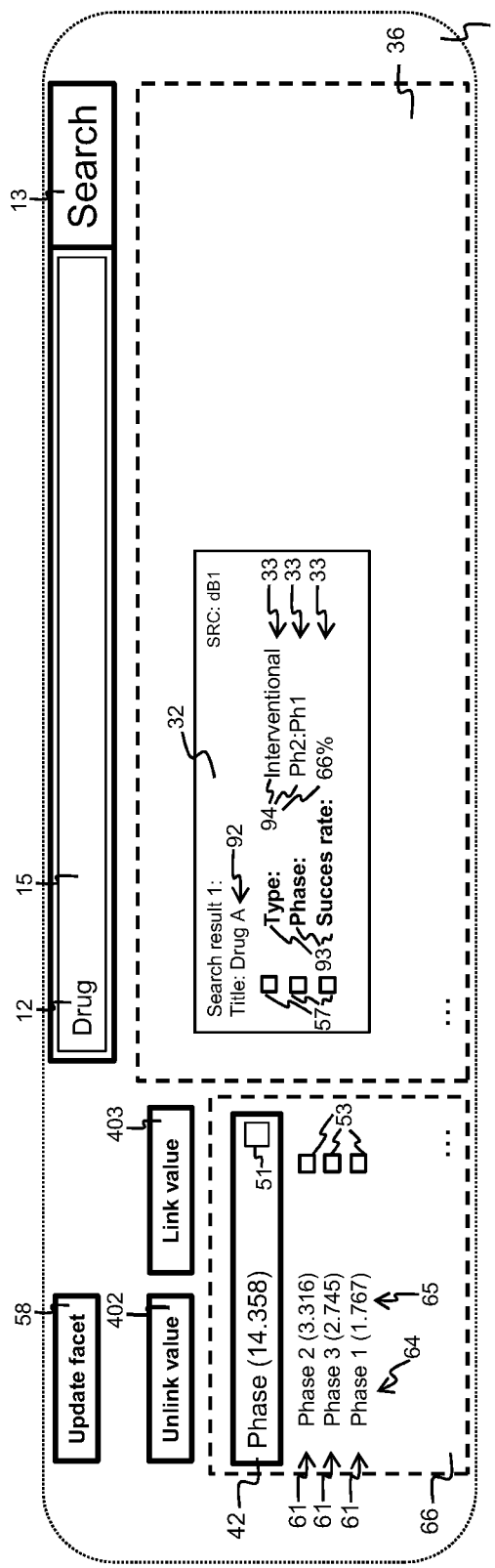

FIGS. 10A, 10B and 10C illustrate a further embodiment of the user interface 80 as illustrated in FIGS. 5-7. The user interface 80 is further provided with a property value unlinking button 402 and a property value linking button 403. Typically with developing database systems, faceted data can be linked in a wrong way. For example, 'Ph2: Ph1' is linked wrongly by the system 1 to the facet category 61 'Phase 1', as this corresponds to a part of the pharmaceutical phase 2.

FIG. 12A shows a set of possible facet category links 610, represented by a facet category linking table 600. This simplified table 600 illustrates how property values 94 internally can be linked with facet categories 61 by means of facet category links 610. Each facet category link 610 comprises a facet identifier 601, a facet category identifier 602, a data source identifier 603, a search result property identifier 604 and a search result property value identifier 605. This table illustrates the (i.e. wrong) link between search result property value 'Ph2: Ph1' with the facet category 'Phase 1'.

A user can make a selection 412 of the checkbox 57 for the search result property value 94 'Ph2: Ph1' of search result property 93 'Phase' (See FIG. 10A) and subsequently press the property value unlinking button 402, therewith giving a property value unlinking command 422 to the data processing system 1. As a result, said facet category link with the property value 'Ph2: Ph1' will be removed. Also, the amount 65 of retrieved search results belonging to the search result facet category 'Phase 1' is updated accordingly (i.e. decreased).

Further, the user can make (or keep) the selection 412 of the checkbox 57 for the property value 94 'Ph2: Ph1' of search result property 93 'Phase', make a selection 411 of the checkbox 53 for the facet category 61 'Phase 2' (See FIG. 10B), and subsequently press the property value linking button 403, therewith giving a property value linking command 423 to the data processing system 1. As a result, a new facet category link 630 will be added to the facet category linking table 600 (See FIG. 12B).

FIG. 10C shows the user interface 80, wherein the amount 65 of retrieved search results belonging to the search result facet category 'Phase 2' is updated accordingly (i.e. increased).

Figure 11:
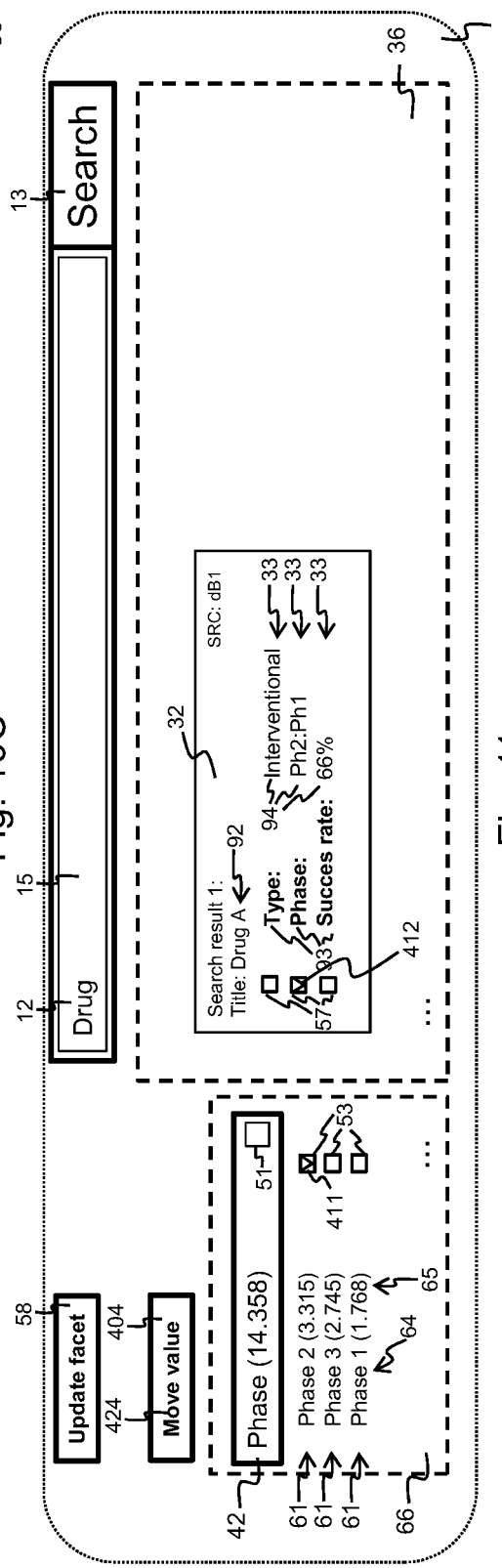

In an alternative embodiment for the user interface 80 of FIGS. 10A-10C, the combination of unlinking and linking a search result property value 94 from or to a facet category 61, can be replaced with a single property value moving button 404. FIG. 11 illustrates this alternative user interface 80. Here, the user makes the selection 412 of the checkbox 57 for the search result property value 'Ph2: Ph1', makes the selection 411 of the checkbox 53 for the facet category 61 'Phase 2' and presses the property value moving button 404, therewith giving a property value moving command 424 to the data processing system 1. This will result in the same addition of the facet category link 630 to the set of facet category links 610 as illustrated in FIG. 12B.

Figure 13:
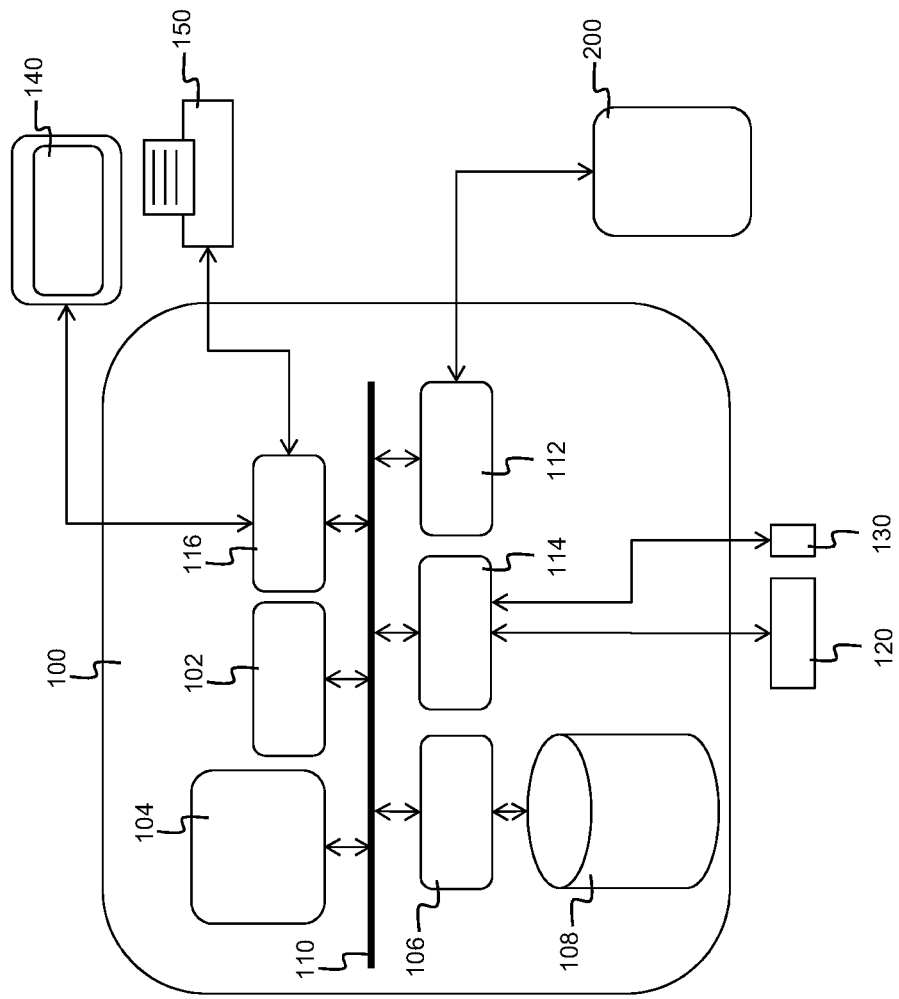
FIG. 13 shows a suitable computing system for hosting the data processing system of FIG. 1.

FIG. 13 shows a suitable computing system 100 for hosting the data processing system of FIG. 1. Computing system 100 may in general be formed as a suitable general purpose computer and comprise a bus 110, a processor 102, a local memory 104, one or more optional input interfaces 114, one or more optional output interfaces 116, a communication interface 112, a storage element interface 106 and one or more storage elements 108. Bus 110 may comprise one or more conductors that permit communication among the components of the computing system. Processor 102 may include any type of conventional processor or microprocessor that interprets and executes programming instructions. Local memory 104 may include a random access memory (RAM) or another type of dynamic storage device that stores information and instructions for execution by processor 102 and/or a read only memory (ROM) or another type of static storage device that stores static information and instructions for use by processor 104. Input interface 114 may comprise one or more conventional mechanisms that permit an operator to input information to the computing device 100, such as a keyboard 120, a mouse 130, a pen, voice recognition and/or biometric mechanisms, etc. Output interface 116 may comprise one or more conventional mechanisms that output information to the operator, such as a display 140, a printer 150, a speaker, etc. Communication interface 112 may comprise any transceiver-like mechanism such as for example two 1 Gb Ethernet interfaces that enables computing system 100 to communicate with other devices and/or systems, for example mechanisms for communicating with one or more other computing systems 200. The communication interface 112 of computing system 100 may be connected to such another computing system by means of a local area network (LAN) or a wide area network (WAN, such as for example the internet, in which case the other computing system 200 may for example comprise a suitable web server. Storage element interface 106 may comprise a storage interface such as for example a Serial Advanced Technology Attachment (SATA) interface or a Small Computer System Interface (SCSI) for connecting bus 110 to one or more storage elements 108, such as one or more local disks, for example 1TB SATA disk drives, and control the reading and writing of data to and/or from these storage elements 108. Although the storage elements 108 above is described as a local disk, in general any other suitable computer-readable media such as a removable magnetic disk, optical storage media such as a CD or DVD,—ROM disk, solid state drives, flash memory cards, . . . could be used.

The components of the data processing system 1, such as the facet module 40, the search result property selection module 81, the search result facet selection module 82, etc. can be implemented as programming instructions stored it local memory 104 of the computing system 100 for execution by its processor 102. Alternatively these components could be stored on the storage element 108 or be accessible from another computing system 200 through the communication interface 112. The same holds for the search results 32,34, search result properties 33,35, search result facets 42, search result facet categories 61, etc., which could also be suitably accessible for processing from the local memory 104, the storage element 108 or another computing system 200, for example comprising a suitable database system 14.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A data processing system for updating search result facets, said data processing system comprising:
   an input module configured to receive a search query;
   a plurality of data sources comprising at least a first data source and a second data source;
   a retrieval module connected to said input module and said data sources and configured to:
      receive from a user via said input module said search query; and
      retrieve a search result list comprising a plurality of first search results from said first data source and a plurality of second search results from said second data source in function of said search query, the first and second search results respectively comprising a plurality of first and second search result properties, each comprising a search result property identifier and a search result property value;
   a facet module connected to said retrieval module, said facet module comprising a facet linking module configured to:
      provide a search result facet list comprising one or more search result facets and one or more search result facet categories per search result facet,
      wherein a search result facet corresponds to a subset of search results of the search result list,
      wherein a search result property identifier of each of said search results is linked with said search result facet via one of a set of predetermined facet links,
      wherein a search result facet category of said search result facet corresponds to one or more search results of said subset, and
      wherein the search result property value of said one or more search results belongs to said facet category, and
      wherein said set of predetermined facet links comprises at least one predetermined first facet link defining a link between a search result facet and a search result property identifier of a first search result property, wherein when said set of predetermined facet links does not comprise a predetermined second facet link defining a link between said search result facet and a search result property identifier of a non-linked second search result property, the data processing system is further configured to:
- determine a selected second search result property in view of said non-linked second search result property;
- determine a selected search result facet in view of said search result facet;
- upon reception of a facet linking command update said one or more facet categories of the selected search result facet in view of the search result property values of the selected second search result property.

2. A data processing system according to claim 1, wherein said data processing system further comprises a search result property selection module for determining a selected second search result property, which module is connected to said retrieval module and facet module and is configured to:
- receive from said user via said input module a property selection of a second search result property of a second search result of said search result list, wherein said second search result property corresponds to said non-linked second search result property.

3. A data processing system according to claim 1, wherein said data processing system further comprises a search result facet selection module for determining a selected search result facet, which module is connected to said facet module and configured to:
- receive from said user via said input module a facet selection of a search result facet of said search result facet list, wherein said search result facet corresponds to said selected search result facet.

4. A data processing system according to claim 3, wherein said facet module further comprises a facet updating module configured to:
- receive from said user via said input module a facet linking command corresponding to said property selection and said facet selection.

5. A data processing system according to claim 1, wherein the facet module is further configured to update said one or more facet categories of the selected search result facet by providing an additional facet link defining a link between the selected search result facet and the search result property identifier of the selected second search result property.

6. A data processing system according to claim 5, wherein said additional facet link is query-specific.

7. A data processing system according to claim 1, wherein said set of predetermined facet links is updated by adding an additional predetermined facet link to said set of predetermined facet links, said additional predetermined facet link defining a link between the selected search result facet and the search result property identifier of the selected second search result property.

8. A data processing system according to claim 7, wherein said set of predetermined facet links is updated by adding said additional predetermined facet link to said set of predetermined facet links, when the number of facet linking commands corresponding to said property selection and said facet selection and received by said facet updating module exceeds a predetermined threshold.

9. A data processing system according to claim 7, wherein said set of predetermined facet links is updated by aggregating additional predetermined facet links to said set of predetermined facet links for a plurality of users of said data processing system.

10. A data processing system according to claim 1, wherein the retrieval module is further configured to:
- receive from a user via said input module a facet category selection of an updated facet category of said search result facet list provided by the facet module;
- receive from said user via said input module a faceted searching command corresponding to said facet category selection;
- retrieve a faceted search result list comprising a plurality of search results from said plurality of data sources in function of said search query and said selected updated facet category.

11. A computer implemented method for updating search result facets comprising the steps of:
- receiving a search query from a user;
- retrieving a search result list comprising a plurality of first search results from a first data source and a plurality of second search results from a second data source in function of said search query, the first and second search results respectively comprising a plurality of first and second search result properties, each comprising a search result property identifier and a search result property value;
- providing a search result facet list comprising one or more search result facets and one or more search result facet categories per search result facet, wherein a search result facet corresponds to a subset of search results of the search result list,
- wherein a search result property identifier of each of said search results is linked with said search result facet via one of a set of predetermined facet links,
- wherein a search result facet category of said search result facet corresponds to one or more search results of said subset, and
- wherein the search result property value of said one or more search results belongs to said facet category, and
- wherein said set of predetermined facet links comprises at least one predetermined first facet link defining a link between a search result facet and a search result property identifier of a first search result property;
- wherein when said set of predetermined facet links does not comprise a predetermined second facet link defining a link between said search result facet and a search result property identifier of a non-linked second search result property:
  - determining a selected second search result property in view of said non-linked second search result property;
  - determining a selected search result facet in view of said search result facet;
  - upon reception of a facet linking command updating said one or more facet categories of the selected search result facet in view of the search result property values of the selected second search result property.

12. A method according to claim 11, further comprising:
- updating one or more facet categories of said selected search result facet by providing an additional facet link defining a link between the selected search result facet and the search result property identifier of the selected second search result property.

13. A method according to claim 11, further comprising:
- receiving from a user a facet category selection of an updated facet category of said search result facet list;
- receiving from said user a faceted searching command corresponding to said facet category selection;

retrieving a faceted search result list comprising a plurality of search results from said plurality of data sources in function of said search query and said selected updated facet category.

14. A method according to claim 11, further comprising:
a user selecting a first facet category of a search result facet;
the user selecting a second facet category of said search result facet;
the user providing a facet category merging command for said first and second facet categories;
merging said first facet category with said second facet category by updating said first facet category in view of the search result property values of said second facet category.

15. A non-transitory computer readable medium comprising computer-executable instructions, which when executed by a data processing system, perform the method according to claim 11.

* * * * *